US011331492B2

(12) United States Patent
Parodi Amaya et al.

(10) Patent No.: US 11,331,492 B2
(45) Date of Patent: May 17, 2022

(54) NEURAL STIMULATOR

(71) Applicants: Jose A. Parodi Amaya, Baton Rouge, LA (US); Edward F Austin, Baton Rouge, LA (US); Jin-Woo Choi, Baton Rouge, LA (US)

(72) Inventors: Jose A. Parodi Amaya, Baton Rouge, LA (US); Edward F Austin, Baton Rouge, LA (US); Jin-Woo Choi, Baton Rouge, LA (US)

(73) Assignee: Board of Supervisors of Louisiana State University and Agricultural and Mechanical College, Baton Rouge, LA (US)

( * ) Notice: Subject to any disclaimer, the term of this patent is extended or adjusted under 35 U.S.C. 154(b) by 0 days.

(21) Appl. No.: 16/862,200

(22) Filed: Apr. 29, 2020

(65) Prior Publication Data

US 2020/0254258 A1    Aug. 13, 2020

Related U.S. Application Data

(63) Continuation of application No. 15/346,391, filed on Nov. 8, 2016, now Pat. No. 10,668,286, which is a
(Continued)

(51) Int. Cl.
*A61N 1/36* (2006.01)
*A61N 1/04* (2006.01)
(Continued)

(52) U.S. Cl.
CPC ....... *A61N 1/36125* (2013.01); *A61N 1/0551* (2013.01); *A61N 1/3787* (2013.01);
(Continued)

(58) Field of Classification Search
CPC .............. A61N 1/0456; A61N 1/0551; A61N 1/36057; A61N 1/36125; A61N 1/36146; A61N 1/36153; A61N 1/3787
See application file for complete search history.

(56) References Cited

U.S. PATENT DOCUMENTS 5,154,172 A * 10/1992 Terry, Jr ............ A61N 1/36053
                                                    323/266
5,702,431 A * 12/1997 Wang ................... A61N 1/3787
                                                    607/33
(Continued)

FOREIGN PATENT DOCUMENTS

WO        2010051317 A1    5/2010

OTHER PUBLICATIONS

Written Opinion from related PCT application No. PCT/US2015/029650 dated Aug. 11, 2015.
(Continued)

*Primary Examiner* — Michael W Kahelin
*Assistant Examiner* — Pamela M. Bays
(74) *Attorney, Agent, or Firm* — John B. Edel; Edel Patents LLC

(57) ABSTRACT

Methods and apparatus are disclosed relating to the stimulating of tissue including nerve tissue based on combinations of capacitors and resistors. Application and removal of voltage to an electrical circuit is taught as part of a method of creating voltage waveforms for nerve and other tissue with such waveforms creating neural signals. The electrical apparatus taught may, include a first electrical node grounded through a first resistor; a second electrical node grounded through a second resistor; a first capacitor connected to both the first electrical node and the second electrical node; a second capacitor separating the second
(Continued)

electrical node from a biological grounding point and direct current sources connected to the two nodes.

10 Claims, 7 Drawing Sheets

Related U.S. Application Data continuation of application No. PCT/US2015/029650, filed on May 7, 2015.

(60) Provisional application No. 61/990,346, filed on May 8, 2014.

(51) Int. Cl.
*A61N 1/378* (2006.01)
*A61N 1/05* (2006.01)

(52) U.S. Cl.
CPC ........ *A61N 1/0456* (2013.01); *A61N 1/36057* (2013.01); *A61N 1/36146* (2013.01); *A61N 1/36153* (2013.01)

(56) References Cited

U.S. PATENT DOCUMENTS

| | | |
|---|---|---|
| 6,321,119 B1 | 11/2001 | Kronberg |
| 2007/0185573 A1 | 8/2007 | Yonezawa |
| 2009/0128154 A1 | 5/2009 | Chu et al. |
| 2011/0309686 A1 | 12/2011 | Scherbenski et al. |
| 2012/0296389 A1 | 11/2012 | Fang et al. |
| 2013/0158622 A1 | 6/2013 | Libbus et al. |

OTHER PUBLICATIONS

Search report from related application EPO 15789965.9, dated Nov. 13, 2017.

* cited by examiner

NEURAL STIMULATOR

This application is a continuation of U.S. application Ser. No. 15/346,391 entitled "Neural Stimulator" filed Nov. 8, 2016 which is a continuation of International Application number PCT/US15/29650 entitled "Neural Stimulator" filed on May 7, 2015 which claims the benefit of U.S. provisional application No. 61/990,346 filed on May 8, 2014 and entitled "Neural Stimulator."

Neural stimulators described herein may be used in the stimulation of nerve and muscle tissues in animals. Certain neural stimulators disclosed herein may be used to stimulate damaged nerve tissue and certain neural stimulators disclosed herein may be used to simulate neural waveforms.

DETAILED DESCRIPTION

The axon initial segment plays a significant role in action potential modulation and contains more Na+, K+, and Ca2+ channels than the rest of the neuron. The enhanced ion channel structure allows for cell-type-specific neural behavior that modulates the amplitude, chance of initiation, rate of decay, rate of rise, and spike duration of action potentials and influences back-propagation into the soma of the neuron. Slow signals (~1.5 s) occurring below the action potential threshold are processed and can induce an action potential at the axon initial segment and action potentials can carry information in an analog fashion. This analog information reflects the intensity of the stimulus that is received by the neuron. These potentials, termed excitatory pre-synaptic potentials have a small amplitude close to 5 mV with a rise time similar to 20 ms, and a half duration in the order of 100 ms.

Inspection of typical action potential, excitatory pre-synaptic potential, and inhibitory post-synaptic potential waveforms shows that these potentials have exponential trends. These potentials may be driven primarily by the flow of ions into and out of the neuron. For action potentials, relative concentrations of ions in the outside of the neuron against the inside determine the resting potential and AP waveform, and affect the behavior of voltage-gated ion channels. For excitatory pre-synaptic potentials and inhibitory post-synaptic potentials, the neurotransmitters from the pre-synaptic cell may affect the behavior of ion channels in the post-synaptic cell which then regulate waveforms in a process similar to the one seen in action potentials. Each ion channel may behave in a discrete way, where ions are allowed to flow in or out at a specific time point and at a determined variable or constant rate. The summation of the effect of all the ion channels in a specific area of the neural membrane is what gives the potentials their characteristic exponential curve. Embodiments described herein reproduce that exponential behavior and may be implemented in in neural stimulators due to that behavior. Each type of ion channel may correspond to a measurable ionic current that affects the output waveform of the overall signal measured through voltage-clamp methodologies. Several ionic currents with exponential trends may determine one specific signal waveform. The action of the ionic currents may be mathematically simplified to the point that only two currents with opposing signs remain. These currents with opposing signs may represent a depolarization and then repolarization event of the nerve membrane.

Figure 1:
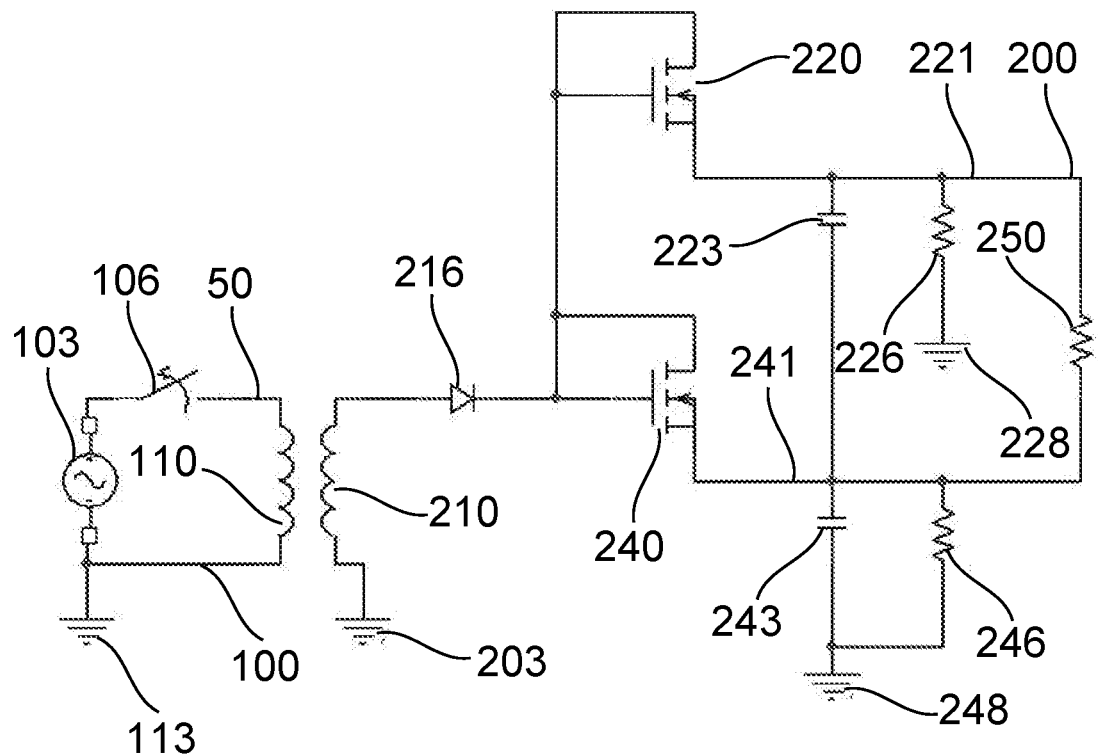
FIG. 1 shows a neural stimulation system.

Equivalent resistances for nerve fibers may range from 8 MΩ to 89 MΩ. Due to the high impedance of nerve cells, the effect of the cell may be assumed to be negligible and does not significantly affect the behavior of the circuit. Waveforms simulated based on the design of FIG. 1 showed waveforms similar to waveforms associated with the ion channels. According to that design, the difference in the potentials between the two capacitors is the source of the stimulation potential. The circuit of FIG. 1 is designed to provide stimulation only when the capacitors are charging or discharging. The circuit provides minimal to no current to the stimulation site when there is a signal powering the circuit; this is due to the fact that the two capacitors are charged to the same voltage. This proves useful whenever the circuit would be in the presence of external signals which could cause undesired behavior. The input voltage or powering signal, can come in various forms including induction coupling, microwave transmission and radio frequency transmission. The powering signal determines the max amplitude of the output stimulation and requires the powering signal to have a minimum amplitude to allow the circuit to function properly. The capacitors and resistors, provide control over the time constant of the stimulation signal, and therefore control the rate of rise and decay of the output waveform. The capacitors also affect the amount of energy that will be transferred into the tissue and the amplitude of the stimulation signal.

Neural stimulation systems consistent with the descriptions herein may take the form of an implantable neural stimulator that has wireless capability, has a passive design, is small scale, and simulates naturally occurring waveforms. Devices such as the devices described herein may, for example, be used to directly stimulate muscle tissue. The circuit design mimics the behavior of ion channels in neurons. In prophetic embodiments, circuits having the general characteristics described herein or as specifically depicted in FIG. 1 would be implemented as an integrated circuit, in a multi-channel implementation, or both.

Example 1

An electrical circuit that utilizes a pair of capacitors was developed in an effort to reproduce the additive effect of these depolarization and repolarization events that result in excitatory pre-synaptic potentials, inhibitory post-synaptic potentials, and action potentials. The waveform resulting from the circuit may be used as a stimulation waveform. The circuit utilizes the potential difference between the two capacitors as the stimulation potential. The same potential is used across each capacitor. By setting the potential across one capacitor as a reference for the other capacitor, the difference in their potentials may be used to produce a stimulation potential. Different time constants are defined for each resistor-capacitor segment in order to model the differential activation of ion channels.

The circuit presented in FIG. 1 contains transistors, which act as an electrical analogue of ion channels. The capacitors may be varied to provide specific rate-of-rise and rate-of-decay for the voltage induced by the current originating from the transistors. The resistors may be selected to be consistent with resistances found in neural stimulation systems. Ionic inward and outward currents are thus modeled in the resistor capacitor segments. The potential difference between the resistor capacitor segments is the stimulation potential of the system. Thus, by varying the capacitance, resistance, input voltage amplitude, and input voltage timing it is possible to generate several diverse waveforms with varying amplitude, duration, and shape.

Referring now to FIG. 1 of the drawings, a Neural stimulator 50 is depicted as having a Signal initiator 100 and a Signal generator 200. Signal initiator 100 may for example include an Alternating current power source 103, a Switch 106, a First magnetic inductance coil 110 and a Ground 113. Signal generator 200 may for example include a Ground 203, a Second magnetic inductance coil 210, a Diode 216, a Top metal-oxide-semiconductor field-effect transistor 220, a First electrical node 221, a Top capacitor 223, a Top resistor 226, a Top ground 228, a Bottom metal-oxide-semiconductor field-effect transistor 240, a Second electrical node 241, a Bottom capacitor 243, a Bottom resistor 246, a Bottom ground 248 and a Stimulation site resistor 250. Components associated with Signal initiator 100 may for example be located outside of a person and components associated with Signal generator 200 may be located inside the body with the components associated with Signal generator 200 being positioned such that voltage waveforms that may be produced by Neural stimulator 50 may initiate actions or other signaling in the body. Various waveforms such as those described herein may be formed by Neural stimulator 50.

Figure 2:
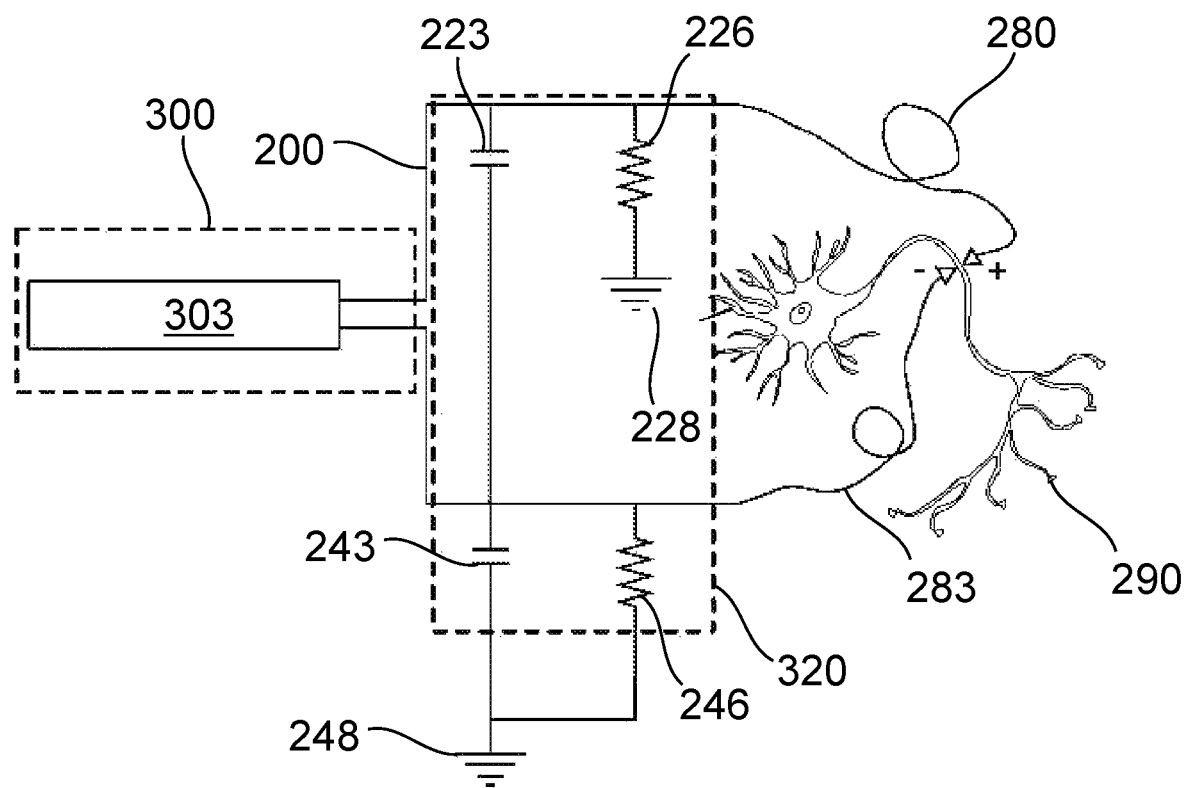
FIG. 2 shows a neural stimulation system configured to act on a nerve.

Referring now to FIG. 2 of the drawings, a Signal generator 200 may include a Top capacitor 223, a Top resistor 226, a Top ground 228, a Bottom capacitor 243, a Bottom resistor 246, a Bottom ground 248, an Input voltage source 300, Input voltage components 303, a Top electrode 280, a Bottom electrode 283 and a Capacitor resistor configuration 320 may be attached to a Nerve 290. The configuration depicted in FIG. 2 may be configured to match the circuitry described in FIG. 1 or it may be powered by other means. Capacitor resistor configuration 320 and the selection of combinations of various capacitors and resistors placed in the configuration of Capacitor resistor configuration 320 may create configurations conducive to the production of particular wave forms useful for neural signaling. Capacitor resistor configuration 320 may be particularly useful for producing excitatory post-synaptic potential waveforms.

Figure 3:
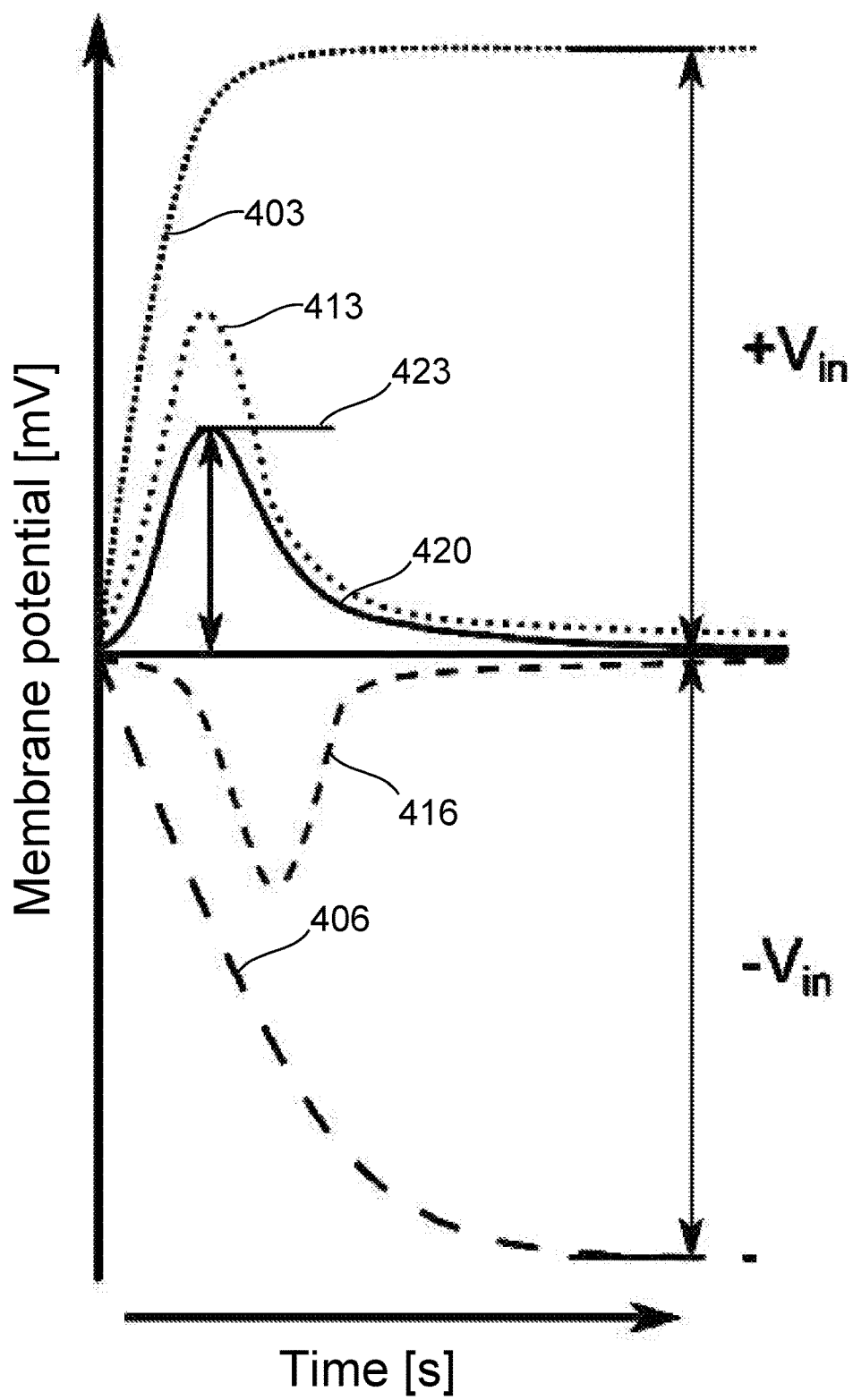
FIG. 3 shows the relationship of a variety of waveforms.

Referring now to FIG. 3 of the drawings, which depicts a variety of waveforms and includes: Top electrode waveform 403, Bottom electrode wave form 406, Sodium ion waveform 413, Potassium ion waveform 416, Combined waveform 420, and Maximum stimulation voltage 423. In FIG. 3, Top electrode waveform 403 represents the voltage of Top electrode 280 over time and Bottom electrode wave form 406 represents the voltage of Bottom electrode 283 over time. Sodium ion waveform 413 represents voltage induced by activity in sodium ion channels and Potassium ion waveform 416 represents the voltage induced by activity in potassium ion channels. Combined waveform 420 represents either the sum of Top electrode waveform 403 and Bottom electrode wave form 406 or it represents the sum of Sodium ion waveform 413 and Potassium ion waveform 416, as those two sums create essentially identical waveforms. Maximum stimulation voltage 423 represents the maximum voltage of the Combined waveform 420.

Figure 4:
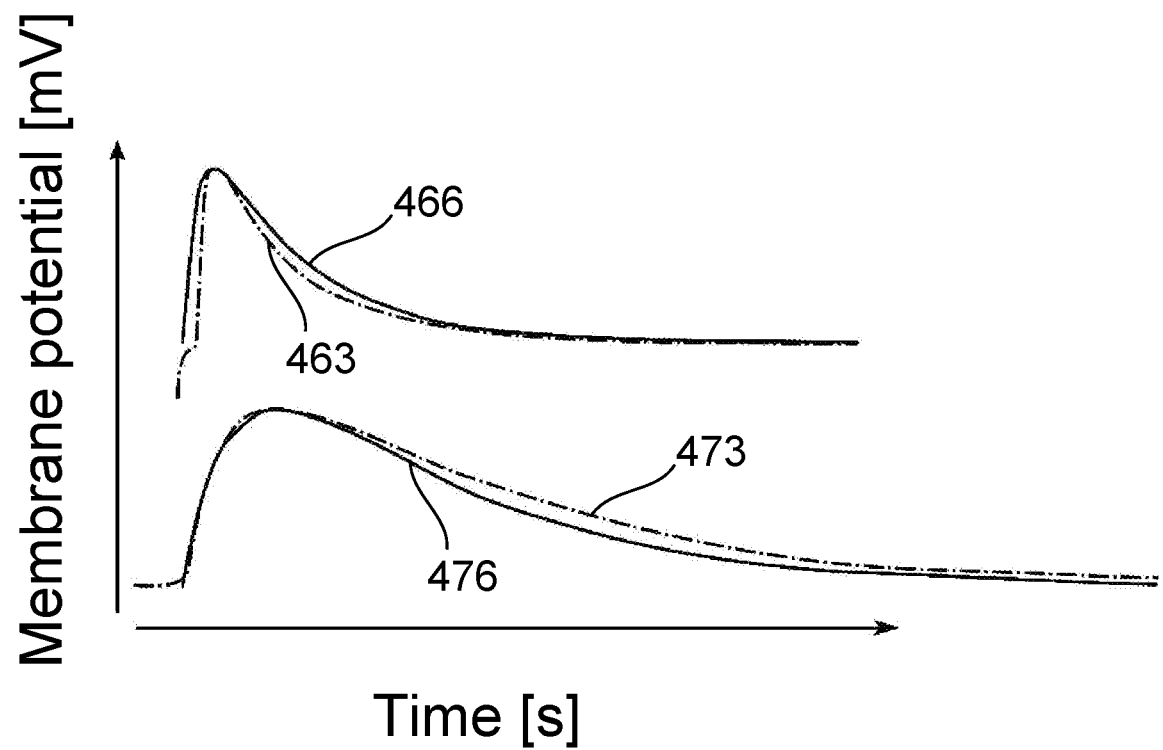
FIG. 4 shows the similarity between simulated voltage potentials and natural voltage potentials.

FIG. 4 of the drawings depicts an Ion channel excitatory post-synaptic potential waveform 463, a Stimulation excitatory post-synaptic potential waveform 466, an Ion channel inhibitory post-synaptic potential waveform 473, and a Stimulation inhibitory post-synaptic potential waveform 476. As can be seen from the figure, the stimulation waveforms produced by embodiments described herein can very closely match the natural ion channel waveforms.

Figure 5:
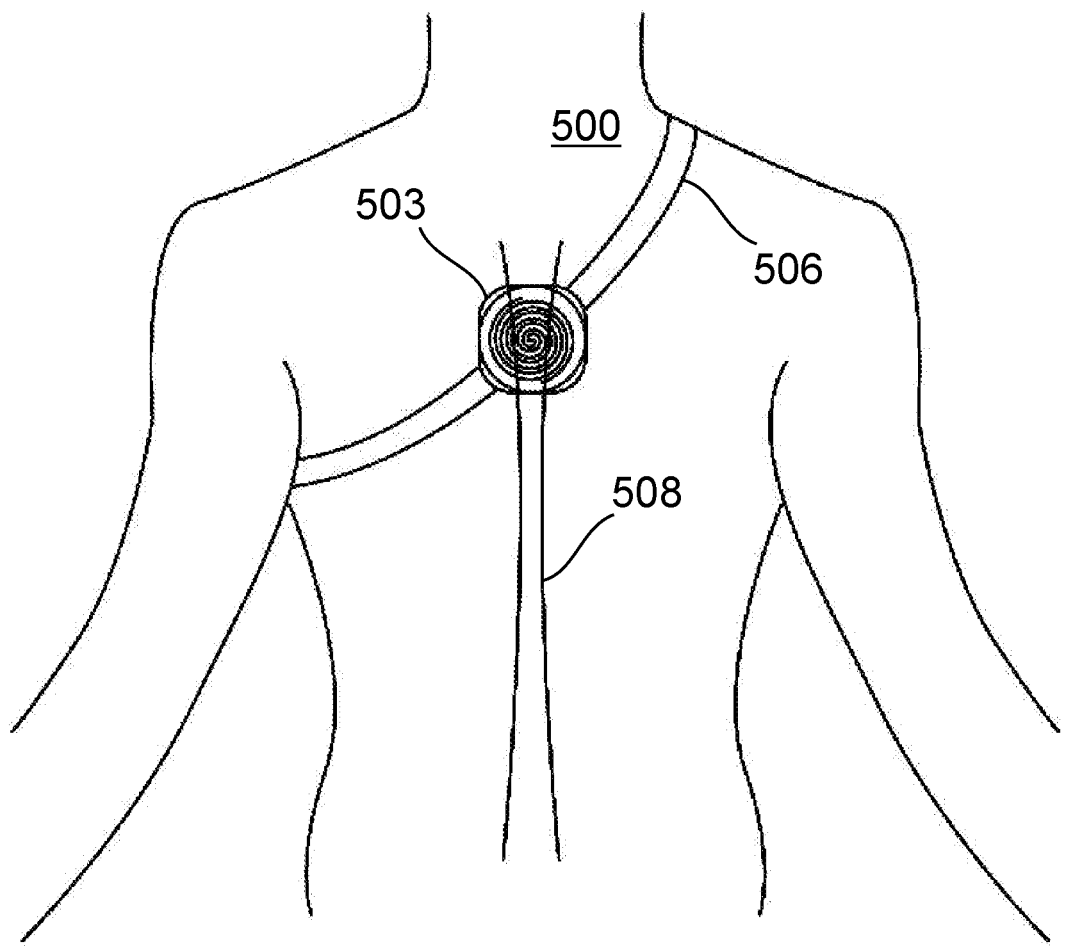
FIG. 5 shows a positioning of an external device.

Referring now to FIG. 5 of the drawings, an External device 503 may be positioned on or near a Person 500 using a Strap 506 to position External device 503 such that it is in proximity to a Signal generator 200 (not shown). Signal generator 200 may, for example, be positioned at the Spinal cord 508 of Person 500.

Figure 6:
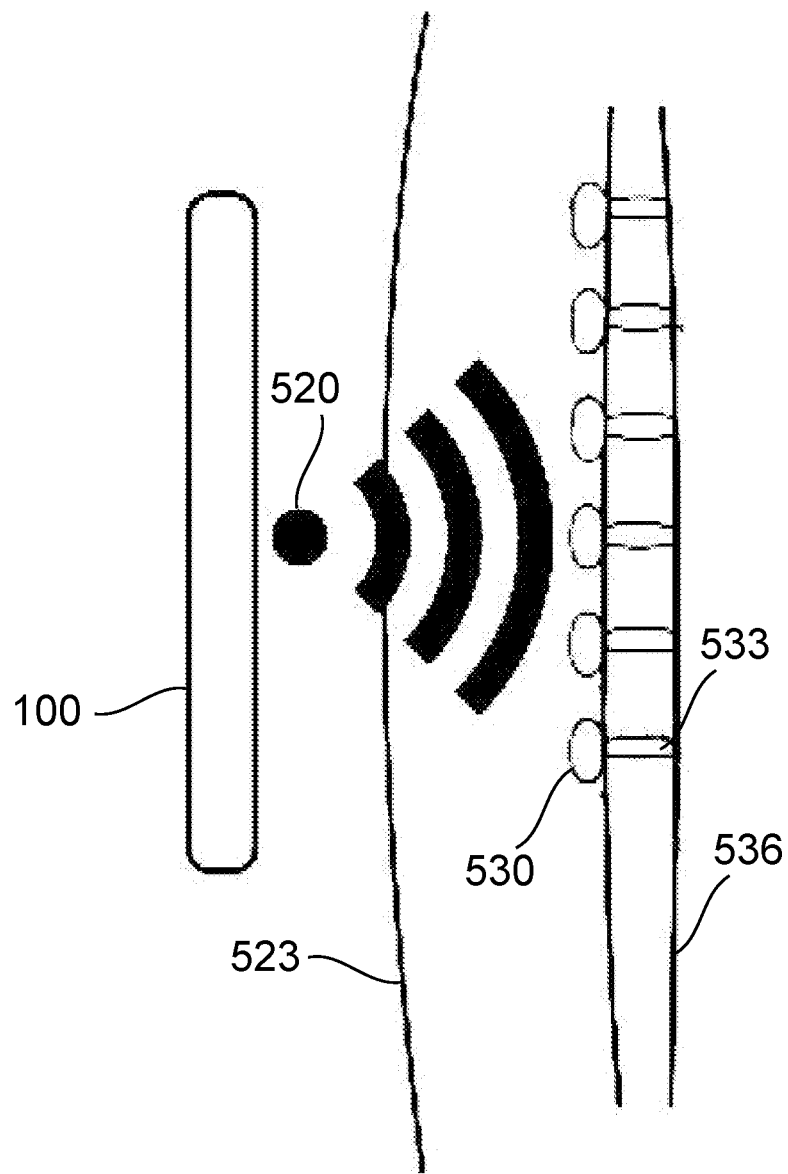
FIG. 6 shows an arrangement for wireless signal control of stimulation devices.

Referring now to FIG. 6 of the drawings, Signal initiator 100 communicates by a Wireless signal 520 to Individual stimulation devices 530 to stimulate Stimulation sites 533 on Spinal nerves 536. Individual stimulation devices 530 may be configured such that varying signals from Signal initiator 100 induce a variety of nervous system responses by way of the particular configurations of the various Individual stimulation devices 530. Wireless signal 520 may act through the Skin 523 of Person 500.

Certain embodiments described herein have features including a passive design and no internal power supply for the portion of Neural stimulator 50 located in the body. Further, the portion of Neural stimulator 50 located in the body may be constructed such that it lacks any form of instruction or control processing. Still further, Signal initiator 100, Signal generator 200 or both may be constructed in significant part by integrated circuit fabrication having few outside components. Signal generator 200 may further operate without wires that connect Signal generator 200 to any device outside the body and may produce one or more of the types of neural signals described herein.

A working prototype of the device was built using bench top components to allow testing of various capacitor values and the behavior of the circuit. Although not constructed in that form, it is contemplated that the circuitry described herein could be implemented in a very-large-scale integration or in a surface mount device. The types of capacitors used were ceramic and thin-film. The tested capacitor values were 9.26±0.005 nF, 21.5±0.05 nF, 32.6±0.05 nF, 47.2±0.05 nF, 50.0±0.05 nF, 92.7±0.05 nF, 146.2±0.05 nF, 465±0.5 nF, 675±0.5 nF, 976±0.5 nF, and 990±0.5 nF. The input signal timing was also varied, with inputs having 3, 4, 5, 8, 12, and 18 Hz input. This was achieved by adjusting the rotating switch input voltage to the values 3.0, 4.0, 5.0, 5.6, 7.0, and 1.0 V, respectively. The input signal was a sine wave 20 KHz, 10 V p-p. The rotating switch methodology affected the time that the signal was charging the circuit, and this time is estimated to be 500 µs±250 µs for 12 Hz, and 20 ms±10 ms for the 3 Hz input timing. Several different waveforms were obtained by varying the capacitance values of the circuit and the timing of the powering signal. The waveforms are characterized by which peak was dominant (primary or secondary), width of the peaks, amplitude of the peaks, and whether or not they resembled action potentials. If a peak was not dominant, it is assumed it does not significantly affect the stimulation potential. In the configuration tested, Top resistor 226 and Bottom resistor 246 were 30 kΩ resistors and Stimulation site resistor 250 was a 1 kΩ resistor. Table 1, below, indicates particular figures showing the characteristic waveforms, the data set from which the signal was obtained, and the corresponding capacitance values.

TABLE 1

Figure 7:
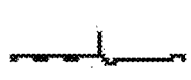
FIG. 7, FIG. 8, FIG. 9, FIG. 10, FIG. 11, FIG. 12, FIG. 13, FIG. 14, FIG. 15, FIG. 16, FIG. 17, FIG. 18, FIG. 19, FIG. 20, FIG. 21, FIG. 22, FIG. 23, FIG. 24, FIG. 25, FIG. 26, FIG. 27, FIG. 28 and FIG. 29 show characteristic waveforms produced by a stimulation device.
Figure 8:
Figure 9:
Figure 10:
Figure 11:
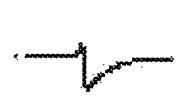
Figure 12:
Figure 13:
Figure 14:
Figure 15:
Figure 16:
Figure 17:
Figure 18:
Figure 19:
Figure 20:
Figure 21:
Figure 22:
Figure 23:
Figure 24:
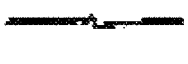
Figure 25:
Figure 26:
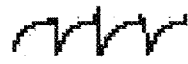
Figure 27:
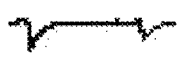
Figure 28:
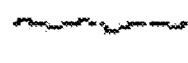
Figure 29:

| FIG. | Data Set | Top Capacitor (nF) | Bottom Capacitor (nF) | Notable Characteristic(s) |
|---|---|---|---|---|
| FIG. 7 | 19 | 9.26 | 146.2 | |
| FIG. 8 | 22 | 9.26 | 675 | Similar to action potential waveform |
| FIG. 9 | 40 | 21.5 | 465 | Predominantly secondary peak |
| FIG. 10 | 16 | 9.26 | 92.7 | Varying width and amplitude for primary and secondary peaks |
| FIG. 11 | 69 | 32.6 | 976 | Predominantly secondary peak |
| FIG. 12 | 148 | 146.2 | 9.26 | Predominantly primary peak |
| FIG. 13 | 149 | 146.2 | 9.26 | Predominantly primary peak |
| FIG. 14 | 84 | 47.2 | 92.7 | Predominantly secondary peak, Varying width and amplitude for primary and secondary peaks |
| FIG. 15 | 88 | 47.2 | 465 | Varying width and amplitude for primary and secondary peaks |
| FIG. 16 | 142 | 94.4 | 465 | Varying width and amplitude for primary and secondary peaks |
| FIG. 17 | 127 | 94.4 | 9.26 | Varying width and amplitude for primary and secondary peaks |
| FIG. 18 | 201 | 990 | 990 | Similar to action potential waveform |
| FIG. 19 | 116 | 50 | 465 | Similar to action potential waveform |
| FIG. 20 | 122 | 50 | 976 | Similar to action potential waveform |
| FIG. 21 | 123 | 50 | 976 | Similar to action potential waveform |
| FIG. 22 | 57 | 21.5 | 47.2 | Predominantly secondary peak |
| FIG. 23 | 61 | 32.6 | 92.7 | Predominantly secondary peak |
| FIG. 24 | 108 | 50 | 92.7 | Varying width and amplitude for primary and secondary peaks |
| FIG. 25 | 23 | 9.26 | 675 | Predominantly secondary peak |
| FIG. 26 | 25 | 9.26 | 976 | Predominantly secondary peak |
| FIG. 27 | 46 | 21.5 | 976 | Predominantly secondary peak |
| FIG. 28 | 103 | 50 | 47.2 | Varying width and amplitude for primary and secondary peaks |
| FIG. 29 | 125 | 50 | 976 | Similar to action potential waveform |

Maximum power consumption of the device was calculated by adding the power dissipated through the diode, metal-oxide-semiconductor field-effect transistors, and resistors during the duration of one stimulation signal. Power dissipated through the resistors in this case was approximated to be 8.2 pW in one stimulation cycle. Power dissipated through the transistors was approximated to be 0.36 mW each, and the diode dissipated an approximate 0.1 mW. The total power dissipated by the system was approximated to be 0.82 mW.

Mathematical analysis of the circuit of FIG. 1 is presented below. The analysis assumes that the signal coming in through the transistors is at a frequency much faster than the discharging rate of the capacitors, and the capacitors are assumed to be constantly charging with negligible ripple due to the high frequency of the input signal. The voltage across the bottom capacitor is $$V_{C2}(t) = V_{in}\left(e^{\frac{-t}{R_2 C_2}}\right)$$

and the voltage for the upper capacitor is $$V_{C1}(t) = V_{in}\left(e^{\frac{-t}{R_1 C_1}}\right)$$

where $V_{in}$ is the amplitude of the input signal. The stimulation voltage is then defined simply as:

$$V_{stim}(t) = V_{C1}(t) - V_{C2}(t)$$

Three factors affect the output signal waveform. The input signal directly affects the maximum output value as it defines the theoretical maximum voltage of an output signal. The input signal can also indirectly affect the shape of the output signal with proper timing. Three input timings can affect the output waveforms depending on when the input signal is turned on or off. The signal can be turned off a long time after it is turned on, turned off quickly after it is turned on, and turned on again quickly after it is turned off. The latter signal timings give rise to stimulation waveforms with two varying peaks. The resistors in the RC segment affect the rate-of-rise and decay of the output signal. The capacitors affect the rate-of-rise and decay, the amplitude of the output waveform, and the shape of the output waveform. For testing purposes, the capacitance was tested across several values ranging from 10 to 1000 nF. The resistance and input voltage signal were kept constant. However, the input voltage signal timing was adjusted when large changes in the time constant occurred in order to properly allow the capacitors to charge.

Electrical circuits described herein may, for example, comprise a first electrical node connected to a first resistor wherein the first electrical node is grounded through the first resistor; a second electrical node connected to a second resistor wherein the second electrical node is grounded through the second resistor; a quantity of tissue having a tissue resistance; a first capacitor connected to the first electrical node; a second capacitor separating the second electrical node from a biological grounding point; a first direct current source electrically connected to the first electrical node and a second direct current source electrically connected to the second electrical node; wherein the quantity of tissue is electrically connected to the first electrical node and wherein the quantity of tissue is electrically connected to the second electrical node. In a related example, the first direct current source may include a first field-effect transistor and the second direct current source may include a second field-effect transistor. In a related example, the first field-effect transistor may be electrically connected to a first coil of a magnetic resonance coupling and the second field-effect transistor may be electrically connected to the first coil of the magnetic resonance coupling. In a related example, the first coil may be located within a human subject.

Methods of stimulating tissue described herein may, for example, comprise implanting an electrical circuit within a mammalian patient wherein the electrical circuit comprises: a first electrical node connected to a first resistor wherein the first electrical node is grounded through the first resistor, a second electrical node connected to a second resistor wherein the second electrical node is grounded through the second resistor, a quantity of tissue having a tissue resistance, a first capacitor connected to the first electrical node, a second capacitor separating the second electrical node from a biological grounding point, a first direct current source electrically connected to the first electrical node and a second direct current source electrically connected to the second electrical node, wherein the quantity of tissue is electrically connected to the first electrical node and wherein the quantity of tissue is electrically connected to the second electrical node; applying a first voltage to the first electrical node from the first direct current source; applying a second voltage to the second electrical node from the second direct current source; ceasing the application of the first voltage to the first electrical node from the first direct current source; ceasing the application of the second voltage to the second electrical node from the second direct current source and creating a voltage waveform at the quantity of tissue sufficient to create a neural signal in the mammalian patient. In a related example, the first voltage is the same as the second voltage. In a further related example, the applying of the first voltage and the applying of the second voltage may occur simultaneously. In a further related example, the ceasing of the application of the first voltage and the ceasing of the application of the second voltage may occur simultaneously. In a further related example, applying a first voltage to the first electrical node and applying a second voltage to the second electrical node may occur without creating a voltage difference between the first electrical node and the second electrical node. In a further related example, the voltage waveform may be a natural waveform associated with the quantity of tissue. In a further related example, the first capacitor, the second capacitor, the first resistor and the second resistor may be arranged and configured to produce a natural waveform associated with the quantity of tissue. In a further related example, the first direct current source and the second direct current source may be powered by a magnetic resonance coupling. In a further related example, the first direct current source and the second direct current source may be powered by radio frequency waves. In a further related example, the first direct current source and the second direct current source may be powered by microwaves. In a further related example, the first direct current source and the second direct current source may be powered by electromagnetic waves. In a further related example, the method may include operating the electrical circuit remotely from outside the mammalian patient.

Electrical circuits described herein may, for example, comprise a first electrical node; a second electrical node; a third electrical node; a fourth electrical node; a first metal-oxide semiconductor field-effect transistor having a first source, a first gate, and a first drain; and a second metal-oxide semiconductor field-effect transistor having a second source, a second gate, and a second drain; such that a quantity of in vivo human tissue is both directly connected to the first electrical node and directly connected to the second electrical node; a first capacitor may be both directly connected to the first electrical node and directly connected to the second electrical node; the first electrical node may be grounded through a first resistor; the third electrical node may be directly connected to the second electrical node by a second capacitor and a second resistor operating in parallel between the second electrical node and the third electrical node; the third electrical node may be grounded; the fourth electrical node may be both directly connected to the first gate and directly connected to the first drain; the fourth electrical node may be both directly connected to the second gate and directly connected to the second drain; the first electrical node may be directly connected to the first source; and the second electrical node may be directly connected to the second source. In a related example, the quantity of in vivo human tissue may contain nerve tissue. In a related example, the electrical circuit may be arranged and configured such that a magnetic resonance coupling electrically connected to the fourth electrical node may cause a voltage waveform at the quantity of in vivo human tissue. In a related example, the electrical circuit may be arranged and configured such that electromagnetic waves received by the circuit may cause a voltage waveform at the quantity of in vivo human tissue. In a related example, the electrical circuit may be arranged and configured such that radio frequency waves received by the circuit may cause a voltage waveform at the quantity of in vivo human tissue. In a related example, the electrical circuit may be arranged and configured such that microwaves received by the circuit may cause a voltage waveform at the quantity of in vivo human tissue.

Electrical circuits described herein may, for example, comprise a first electrical node; a second electrical node; a third electrical node; a fourth electrical node; a first metal-oxide semiconductor field-effect transistor having a first source, a first gate, and a first drain; and a second metal-oxide semiconductor field-effect transistor having a second source, a second gate, and a second drain; such that a quantity of in vivo human tissue may be both directly connected to the first electrical node and directly connected to the second electrical node; a first capacitor may be both directly connected to the first electrical node and directly connected to the second electrical node; the first electrical node may be grounded through a first resistor; the third electrical node may be directly connected to the second electrical node by a second capacitor and a second resistor operating in parallel between the second electrical node and the third electrical node; the third electrical node may be grounded; the fourth electrical node may be directly connected to the first metal-oxide semiconductor field-effect transistor; the fourth electrical node may be directly connected to the second metal-oxide semiconductor field-effect transistor; the first electrical node may be directly connected to the first metal-oxide semiconductor field-effect transistor; the second electrical node may be directly connected to the second metal-oxide semiconductor field-effect transistor; and the fourth electrical node may be connected to a cathode of a diode. In a related example, the diode may be directly electrically connected to a magnetic inductance coil. In a related example, the electrical circuit may be arranged and configured such that a period of current flow through the diode causes a voltage waveform at the quantity of in vivo human tissue. In a related example, the quantity of in vivo human tissue may comprise nerve tissue. In a related example, the electrical circuit may be arranged and configured such that a magnetic resonance coupling electrically connected to the fourth electrical node may cause a voltage waveform at the quantity of in vivo human tissue. In a related example, the electrical circuit may be arranged and configured such that electromagnetic waves received by the circuit may cause a voltage waveform at the quantity of in vivo human tissue. In a related example, the electrical circuit may be arranged and configured such that radio frequency waves received by the circuit may cause a voltage waveform at the quantity of in vivo human tissue. In a related example, the electrical circuit may be arranged and configured such that microwaves received by the circuit may cause a voltage waveform at the quantity of in vivo human tissue.

The above-described embodiments have a number of independently useful individual features that have particular utility when used in combination with one another including combinations of features from embodiments described separately. There are, of course, other alternate embodiments which are obvious from the foregoing descriptions of the invention, which are intended to be included within the scope of the invention, as defined by the following claims.

We claim:

1. An electrical apparatus comprising:
   a. a first electrical node;
   b. a second electrical node;
   c. a third electrical node;
   d. a fourth electrical node;
   e. a first metal-oxide semiconductor field-effect transistor having a first source, a first gate, and a first drain; and
   f. a second metal-oxide semiconductor field-effect transistor having a second source, a second gate, and a second drain;
   g. wherein the first electrical node and the second electrical node are arranged and configured to simultaneously contact a quantity of tissue;
   h. wherein a first capacitor is both directly connected to the first electrical node and directly connected to the second electrical node;
   i. wherein the first electrical node is directly connected to a first resistor which is grounded;
   j. wherein the third electrical node is directly connected to the second electrical node by a second capacitor and a second resistor operating in parallel between the second electrical node and the third electrical node;
   k. wherein the third electrical node is grounded;
   l. wherein the fourth electrical node is both directly connected to the first gate and directly connected to the first drain;
   m. wherein the fourth electrical node is both directly connected to the second gate and directly connected to the second drain;
   n. wherein the first electrical node is directly connected to the first source; and
   o. wherein the second electrical node is directly connected to the second source.

2. The electrical apparatus of claim 1 wherein the electrical apparatus is arranged and configured such that a magnetic resonance coupling electrically connected to the fourth electrical node is configured to cause a voltage waveform between the first electrical node and the second electrical node.

3. The electrical apparatus of claim 1 wherein the electrical apparatus is arranged and configured to receive electromagnetic waves to cause a voltage waveform between the first electrical node and the second electrical node.

4. The electrical apparatus of claim 1 wherein the electrical apparatus is arranged and configured to receive microwaves to cause a voltage waveform between the first electrical node and the second electrical node.

5. An electrical apparatus comprising:
   a. a first electrical node;
   b. a second electrical node;
   c. a third electrical node;
   d. a fourth electrical node;
   e. a first metal-oxide semiconductor field-effect transistor having a first source, a first gate, and a first drain; and
   f. a second metal-oxide semiconductor field-effect transistor having a second source, a second gate, and a second drain;
   g. wherein the first electrical node and to the second electrical node are arranged and configured to simultaneously contact a quantity of tissue;
   h. wherein a first capacitor is both directly connected to the first electrical node and directly connected to the second electrical node;
   i. wherein the first electrical node is directly connected to a first resistor which is grounded;
   j. wherein the third electrical node is directly connected to the second electrical node by a second capacitor and a second resistor operating in parallel between the second electrical node and the third electrical node;
   k. wherein the third electrical node is grounded;
   l. wherein the fourth electrical node is directly connected to the first metal-oxide semiconductor field-effect transistor;
   m. wherein the fourth electrical node is directly connected to the second metal-oxide semiconductor field-effect transistor;
   n. wherein the first electrical node is directly connected to the first metal-oxide semiconductor field-effect transistor;
   o. wherein the second electrical node is directly connected to the second metal-oxide semiconductor field-effect transistor;
   p. and wherein the fourth electrical node is connected to a cathode of a diode.

6. The electrical apparatus of claim 5 wherein the diode is directly electrically connected to a magnetic inductance coil.

7. The electrical apparatus of claim 5 wherein the electrical apparatus is arranged and configured such that a period of current flow through the diode causes a voltage waveform between the first electrical node and the second electrical node.

8. The electrical apparatus of claim 5 wherein the electrical apparatus is arranged and configured such that a magnetic resonance coupling electrically connected to the fourth electrical node is configured to cause a voltage waveform between the first electrical node and the second electrical node.

9. The electrical apparatus of claim 5 wherein the electrical apparatus is arranged and configured to receive electromagnetic waves to cause a voltage waveform between the first electrical node and the second electrical node.

10. The electrical apparatus of claim 5 wherein the electrical apparatus is arranged and configured to receive microwaves to cause a voltage waveform between the first electrical node and the second electrical node.

* * * * *